United States Patent [19]
Mafrand et al.

[11] 4,339,450
[45] Jul. 13, 1982

[54] AMINOPROPAN-2-01 DERIVATIVES AND PHARMACEUTICAL COMPOSITIONS

[75] Inventors: Jean P. Mafrand, Toulouse; Jean Courregelongue, Garonne, both of France

[73] Assignee: Sanofi, Paris, France

[21] Appl. No.: 219,213

[22] Filed: Dec. 22, 1980

[30] Foreign Application Priority Data

Dec. 21, 1979 [FR] France ............................. 79 31402

[51] Int. Cl.³ .................. A61K 31/535; A61K 31/38; C07D 413/12; C07D 333/54
[52] U.S. Cl. .......................... 424/248.51; 424/246; 424/250; 424/267; 424/263; 424/274; 424/275; 544/61; 544/146; 544/376; 546/202; 546/274; 549/57; 260/330.3; 548/525

[58] Field of Search ........................ 544/61, 146, 376; 546/202, 274; 549/57; 260/326.5 SA, 330.3; 424/246, 248.51, 250, 267, 274, 263, 275

[56] References Cited

PUBLICATIONS

Kloetzel et al., *J. Org. Chem.* 18, (1953), pp. 1511–1515.
Cagniant et al., *Bull. Soc. Chem.* (France) (1955), 680–685.
Sam et al., *J. Pharm. Sci.*, 52, (1963), pp. 898–901.

*Primary Examiner*—Robert W. Ramsuer
*Attorney, Agent, or Firm*—Weiser, Stapler & Spivak

[57] ABSTRACT

Derivatives of 1-aminopropan-2-ol which are useful in the treatment and control of cardiac disorders in warm-blooded mammals. The process of manufacture and pharmaceutical compositions.

47 Claims, No Drawings

AMINOPROPAN-2-01 DERIVATIVES AND PHARMACEUTICAL COMPOSITIONS

The present invention is concerned with new derivatives of 1-aminopropan-2-ol, with the preparations and with the use thereof in human and veterinary medicine.

The new compounds of the present invention have the following general formulae:

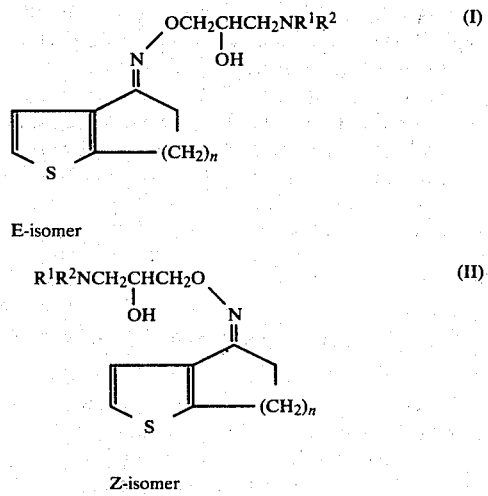

E-isomer

Z-isomer wherein $R^1$ and $R^2$, which can be the same or different, are hydrogen atoms, straight-chained or branched alkyl radicals containing up to 10 carbon atoms; mono- or polycyclic cycloalkyl radicals containing up to 14 carbon atoms and optionally substituted one or more times by alkyl radicals containing up to 4 carbon atoms; straight-chained or branched alkenyl radicals containing 3 to 7 carbon atoms; straight-chained or branched alkynyl radicals containing 3 to 7 carbon atoms; aryl radicals or aralkyl radicals containing up to 4 carbon atoms in the alkyl moiety, the aromatic nuclei being optionally substituted one or more times by halogen atoms or hydroxyl groups or alkyl or alkoxy radicals containing up to 4 carbon atoms; heteraryl radicals or heteroaralkyl radicals containing up to 4 carbon atoms in the alkyl moiety; aminoalkyl radicals containing up to 4 carbon atoms and optionally mono- or di-substituted on the nitrogen atom by alkyl radicals containing up to 4 carbon atoms; alkoxyalkyl radicals; aralkoxyalkyl radicals; or aryloxyalkyl radicals; or $R^1$ and $R^2$, together with the nitrogen atom to which they are attached, form a heterocyclic radical containing 5 to 7 ring members and optionally containing another heteroatom selected from oxygen, sulphur and nitrogen, the nitrogen being optionally substituted by an alkyl radical containing up to 6 carbon atoms or by an aryl, aralkyl or aroyl radical, the aromatic nucleus of which is optionally mono- or polysubstituted by halogen atoms or hydroxyl groups or alkyl or alkoxy radicals containing up to 4 carbon atoms; and n is 1, 2 or 3; and the addition salts thereof which pharmaceutically-acceptable inorganic or organic acids.

In the above definitions, the term "aryl" more particularly denotes an unsaturated monocyclic or polycyclic radical, for example a phenyl radical and the term "heteroaryl" more particularly denotes an unsaturated mono- or polycyclic radical, for example a pyridyl radical. The term "aralkyl" likewise denotes, for example, a benzyl, phenethyl or benzhydryl radical.

By the term "saturated heterocyclic radical", there is understood, more particularly, radicals such as pyrrolidino, piperidino, morpholino and the like radicals.

The straight-chained or branched alkenyl radicals are, in particular, $\alpha,\alpha$-dialkylallyl radicals and the straight-chained or branched alkynyl radicals are preferably $\alpha,\alpha$-dialkylpropynyl radicals.

A preferred group of compounds according to the present invention have the above-given general formulae (I) and (II), wherein $R^1$ and $R^2$, which may be the same or different, are hydrogen atoms; straight-chained or branched alkyl radicals containing up to 8 carbon atoms; monocyclic cycloalkyl radicals containing up to 12 carbon atoms or adamantyl radicals; $\alpha,\alpha$-dialkylpropynyl radicals, each alkyl moiety of which contains up to 4 carbon atoms; phenylalkyl radicals, the alkyl moiety of which contains up to 4 carbon atoms and the phenyl nucleus of which is optionally substituted one or more times by alkoxy radicals containing up to 4 carbon atoms; pyridylalkyl radicals containing up to 4 carbon atoms in the alkyl moiety; or dialkylaminoalkyl radicals, each alkyl moiety of which contains up to 4 carbon atoms; or $R^1$ and $R^2$, together with the nitrogen atom to which they are attached, form a pyrrolidino, morpholino or piperidino radical, the latter optionally being substituted on the other nitrogen atom by an alkyl radical containing up to 4 carbon atoms or by a benzyl radical; and n is 1, 2 or 3; and the addition salts thereof with pharmaceutically-acceptable inorganic or organic acids.

The compounds of general formulae (I) and (II) contain an asymmetric carbon atom and can, therefore, exist in the form of optical isomers which can be obtained by conventional methods. The present invention relates to both the pure stereoisomers and to mixtures thereof.

The present invention also provides a process for the preparation of compounds of general formulae (I) and (II).

This process comprises:

(a) condensing an oxime of the general formula:

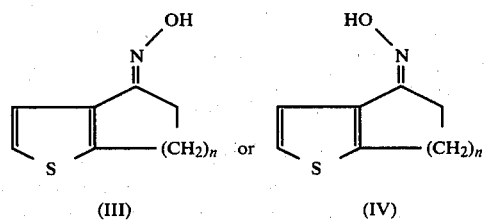

in which n has the same meaning as above, with an epihalohydrin in an inert solvent, in the presence of a base and at a temperature of from 10° C. to the boiling point of the solvent, to give a compound of the general formula:

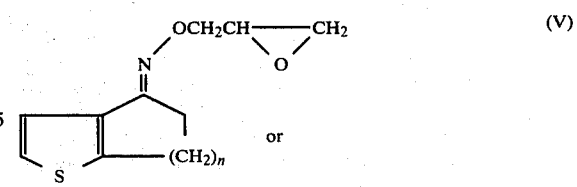

or

-continued

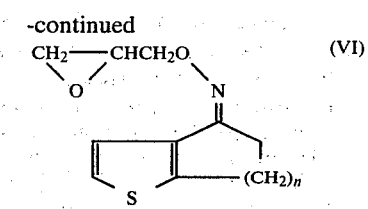

in which n has the same meaning as above, and (b) condensing a compound of general formula (V) or (VI) with an amine of the general formula HNR$^1$R$^2$, in which R$^1$ and R$^2$ have the same meanings as above, in an inert solvent and at a temperature of from 10° C. to the boiling point of the solvent, to give, respectively, a compound of general formula (I) or (II).

The condensation reaction in stage (a) is preferably carried out using epichlorohydrin in an inert solvent selected from dimethylformamide, methanol and ethanol, preferably in the presence of an alkali metal carbonate, such as potassium carbonate, as the base.

In the condensation reaction of stage (b), a lower alkanol, such as ethanol or methanol, is preferably used as the inert solvent and the reaction is advantageously carried out with the use of an excess of amine.

The compound of general formula (III), in which n is 2, has already been described (see M. C. Kloetzel, J. E. Little, Jr. and D. M. Frisch, J. Org. Chem., 18, 1511/1953). However, its preparation is always accompanied by a certain amount of its isomer (IV) (n=2), which may be isolated by chromatography on a silica gel column (eluant: toluene/ethyl acetate 9/1 v/v). After recrystallisation from diisopropyl ether, it melts at 140° C.

The oxime of general formula (III), in which n is 3, is also known (see P. Cagniant and D. Cagniant, Bull. Soc. Chim. France, 1955, 680). A small quantity of its isomer of general formula (IV), which was not mentioned in the above literature reference, was obtained in the reaction mixture and may be isolated by chromatography on a silica gel column (eluant: toluene). It has a melting point of 68° C.

The oxime of general formula (III), in which n is 1, has been prepared starting from the corresponding ketone, which is described in the literature (see J. Sam and A. C. Thompson, J. Pharm. Sci., 52, 898/1963). Its isomer of general formula (IV), in which n is 1, could not be detected in the reaction mixture.

The following Examples are given for the purpose of illustrating the present invention:

EXAMPLE 1

E-4-(3-tert.-Butylamino-2-hydroxypropoxy)-imino-4,5,6,7-tetrahydrobenzo[b]thiophene (I) (R$^1$=H, R$^2$=tBu; n=2)

(a) Preparation of the E- or Z-isomer of 4-(2,3-epoxypropoxy)-imino-4,5,6,7-tetrahydrobenzo[b]thiophene A mixture of 100 g. (0.60 mol) of the E-oxime of 4-oxo-4,5,6,7-tetrahydrobenzo[b]thiophene, 330 g. (3.6 mols) of epichlorohydrin and 391.2 g. (2.8 mols) of potassium carbonate in one liter of dimethylformamide is heated to 110° C. for 6 hours.

After filtering off the mineral salts and evaporating the filtrate to dryness, the brown oil obtained is dissolved in ethyl acetate. The organic phase is washed with water, dried over anhydrous sodium sulphate and evaporated to dryness. The residual oil is chromatographed on a silica-gel column (eluant: toluene/ethyl acetate 95/5 v/v). The E-isomer is obtained in the form of an orange oil (yield: 83% of theory). The Z-isomer is prepared in the same manner, starting from the isolated Z-oxime; greenish oil; yield: 56% of theory.

(b) Preparation of E-4-(2-hydroxy-3-tert.-butylaminopropoxy)-imino-4,5,6,7-tetrahydrobenzo[b]thiophene A solution of 8 g. (0.036 mol) of E-4-(2,3-epoxypropoxy)-imino-4,5,6,7-tetrahydrobenzo[b]thiophene and 5.3 g. (2 equivalents) of tert.-butylamine in 100 cc. of ethanol is heated under reflux for 4 hours. The mixture is evaporated to dryness and the residual oil is chromatographed on a silica-gel column (eluant: methylene chloride/methanol 9/1 v/v). The product obtained is converted into the maleate: white crystals; m.p. 148° C. (recrystallised from isopropyl alcohol/diisopropyl ether); yield: 55.5% of theory.

EXAMPLE 2

E-4-(2-Hydroxy-3-isopropylaminopropoxy)-imino-4,5,6,7-tetrahydrobenzo[b]thiophene (I) (R$^1$=H, R$^2$=iPr; n=2)

This compound is prepared by the procedure described in Example 1 by condensing E-4-(2,3-epoxypropoxy)-imino-4,5,6,7-tetrahydrobenzo[b]thiophene with isopropylamine. Oxalate: white crystals; m.p. 150° C. (recrystallised from isopropyl alcohol/diisopropyl ether); yield: 62.5% of theory.

EXAMPLE 3

E-4-(3-Cyclohexylamino-2-hydroxypropoxy)-imino-4,5,6,7-tetrahydrobenzo[b]thiophene (I) (R$^1$=H, R$^2$=cyclohexyl; n=2)

This compound is prepared by the procedure described in Example 1 by condensing E-4-(2,3-epoxypropoxy)-imino-4,5,6,7-tetrahydrobenzo[b]thiophene with cyclohexylamine. Maleate: white crystals; m.p. 138° C. (recrystallised from isopropyl alcohol); yield: 77% of theory.

EXAMPLE 4

E-4-[3-(Adamanant-1-yl)-amino-2-hydroxypropoxy]-imino-4,5,6,7-tetrahydrobenzo[b]thiophene (I) (R$^1$=H, R$^2$=adamantyl; n=2)

This compound is prepared by the procedure described in Example 1 by condensing E-4-(2,3-epoxypropoxy)-imino-4,5,6,7-tetrahydrobenzo[b]thiophene with 1-aminoadamantane. Maleate: white crystals; m.p. 204° C. (recrystallized from ethanol); yield: 56% of theory.

EXAMPLE 5

E-4-(3-Cyclododecylamino-2-hydroxypropoxy)-imino-4,5,6,7-tetrahydrobenzo[b]thiophene (I) (R$^1$=H, R$^2$=cyclododecyl; n=2)

This compound is prepared by the procedure described in Example 1 by condensing E-4-(2,3-epoxypropoxy)imino-4,5,6,7-tetrahydrobenzo[b]thiophene with cyclododecylamine. Maleate: white crystals; m.p. 164° C. (recrystallised from isopropyl alcohol); yield: 70% of theory.

EXAMPLE 6

E-4-[3-(1,1-Diethylprop-2-ynyl)-amino-2-hydroxy-propoxy]imino-4,5,6,7-tetrahydrobenzo[b]thiophene (I) ($R^1$=H, $R^2$=—C($C_2H_5$)$_2$C≡CH; n=2)

This compound is prepared by the procedure described in Example 1 by condensing E-4-(2,3-epoxypropoxy)imino-4,5,6,7-tetrahydrobenzo[b]thiophene with 2,2-diethyl-propargylamine. Oxalate: white crystals; m.p. 150° C. (recrystallised from isopropyl alcohol); yield: 81.5% of theory.

EXAMPLE 7

E-4-[2-Hydroxy-3-(4-methylpiperazin-1-yl)-propoxy]imino-4,5,6,7-tetrahydrobenzo[b]thiophene (I)

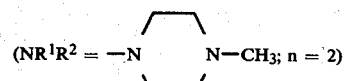

This compound is prepared by the procedure described in Example 1 by condensing E-4-(2,3-epoxypropoxy)imino-4,5,6,7-tetrahydrobenzo[b]thiophene with 1-methylpiperazine. Dioxalate: white crystals; m.p. 198° C. (recrystallised from methanol/water); yield: 66% of theory.

EXAMPLE 8

E-4-[2-Hydroxy-3-(pyrrolidin-1-yl)-propoxy]imino-4,5,6,7-tetrahydrobenzo[b]thiophene (I)

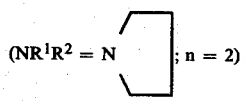

This compound is prepared by the procedure described in Example 1 by condensing E-4-(2,3-epoxypropoxy)imino-4,5,6,7-tetrahydrobenzo[b]thiophene with pyrrolidine. Oxalate: white crystals; m.p. 136° C. (recrystallised from isopropyl alcohol); yield: 77.5% of theory.

EXAMPLE 9

E-4-(2-Hydroxy-3-morpholinopropoxy)-imino-4,5,6,7-tetrahydrobenzo[b]thiophene (I)

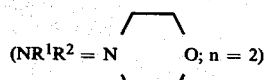

This compound is prepared by the procedure described in Example 1 by condensing E-4-(2,3-epoxypropoxy)imino-4,5,6,7-tetrahydrobenzo[b]thiophene with morpholine. Oxalate: white crystals; m.p. 152° C. (recrystallised from isopropyl alcohol/methanol); yield: 76% of theory.

EXAMPLE 10

E-4-[2-Hydroxy-3-(3,4-dimethoxyphenethylamino)-propoxy]imino-4,5,6,7-tetrahydrobenzo[b]thiophene (I) ($R^1$=H, $R^2$=3,4-di—MeO—$C_6H_3$—($CH_2$)$_2$; n=2)

This compound is prepared by the procedure described in Example 1 by condensing 3,4-dimethoxyphenethylamine with E-4-(2,3-epoxypropoxy)-imino-4,5,6,7-tetrahydrobenzo[b]thiophene. Oxalate: white crystals; m.p. 167° C. (recrystallised from ethanol); yield: 48% of theory. Hydrochloride: white crystals; m.p. 134° C. (recrystallised from isopropyl alcohol); yield: 23.5% of theory.

EXAMPLE 11

E-4-(3-Benzylamino-2-hydroxypropoxy)-imino-4,5,6,7-tetrahydrobenzo[b]thiophene (I) ($R^1$=H, $R^2$=$C_6H_5$—$CH_2$; n=2)

This compound is prepared by the procedure described in Example 1 by condensing E-4-(2,3-epoxypropoxy)imino-4,5,6,7-tetrahydrobenzo[b]thiophene with benzylamine. Oxalate: white crystals; m.p. 207° C. (recrystallised from isopropyl alcohol); yield: 36% of theory.

EXAMPLE 12

E-4-(2-Hydroxy-3-piperidinopropoxy)-imino-4,5,6,7-tetrahydrobenzo[b]thiophene (I)

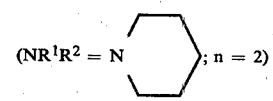

This compound is prepared by the procedure described in Example 1 by condensing E-4-(2,3-epoxypropoxy)imino-4,5,6,7-tetrahydrobenzo[b]thiophene with piperidine. Hemifumarate- white crystals; m.p. 146° C. (recrystallised from isopropyl alcohol); yield: 66% of theory.

EXAMPLE 13

E-4-[3-(4-Benzylpiperazin-1-yl)-2-hydroxypropoxy]-imino-4,5,6,7-tetrahydrobenzo[b]thiophene (I)

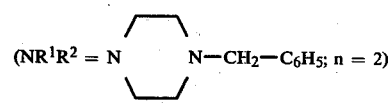

This compound is prepared by the procedure described in Example 1 by condensing E-4-(2,3-epoxypropoxy)imino-4,5,6,7-tetrahydrobenzo[b]thiophene with 1-benzylpiperazine. Dimaleate: white crystals; m.p. 210° C. (recrystallised from methanol/water); yield: 46% of theory.

EXAMPLE 14

E-4-(2-Hydroxy-3-octylaminopropoxy)-imino-4,5,6,7-tetrahydrobenzo[b]thiophene (I) ($R^1$=H, $R^2$=octyl; n=2)

This compound is prepared by the procedure described in Example 1 by condensing E-4-(2,3-epoxypropoxy)imino-4,5,6,7-tetrahydrobenzo[b]thiophene with octylamine. Oxalate: white crystals; m.p. 152° C. (recrystallised from isopropyl alcohol); yield: 43% of theory.

EXAMPLE 15

E-4-[2-Hydroxy-3-(pyrid-3-ylmethyl)-aminopropoxy]imino-4,5,6,7-tetrahydrobenzo[b]thiophene (I) (R$^1$=H,

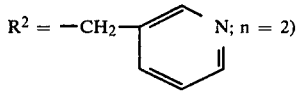

R$^2$ = —CH$_2$— (pyridyl); n = 2)

This compound is prepared by the procedure described in Example 1 by condensing E-4-(2,3-epoxypropoxy)imino-4,5,6,7-tetrahydrobenzo[b]thiophene with picolylamine. Dioxalate: beige crystals; m.p. 214° C. (recrystallised from methanol); yield: 30% of theory.

EXAMPLE 16

E-4-(3-Cyclopentylamino-2-hydroxypropoxy)-imino-4,5,6,7-tetrahydrobenzo[b]thiophene (I) R$^1$=H, R$^2$=cyclopentyl; n=2)

This compound is prepared by the procedure described in Example 1 by condensing E-4-(2,3-epoxypropoxy)imino-4,5,6,7-tetrahydrobenzo[b]thiophene with cyclopentylamine. Maleate: white crystals; m.p. 120° C. (recrystallised from isopropyl alcohol); yield 64% of theory.

EXAMPLE 17

E-4-[3-(1,1-Dimethylprop-2-ynyl)-amino-2-hydroxypropoxy]imino-4,5,6,7-tetrahydrobenzo[b]thiophene (I) (R$^1$=H, R$^2$=C(CH$_3$)$_2$C≡CH; n=2)

This compound is prepared by the procedure described in Example 1 by condensing E-4-(2,3-epoxypropoxy)imino-4,5,6,7-tetrahydrobenzo[b]thiophene with 2,2-dimethylpropargylamine. Hemioxalate: white crystals; m.p. 204° C. (recrystallised from methanol/water); yield: 44% of theory.

EXAMPLE 18

E-4-[2-Hydroxy-3-(β-dimethylaminoethylamino)-propoxy]imino-4,5,6,7-tetrahydrobenzo[b]thiophene (I) (R$^1$=H, R$^2$=(CH$_3$)$_2$N—(CH$_2$)$_2$; n=2).

This compound is prepared by the procedure described in Example 1 by condensing E-4-(2,3-epoxypropoxy)imino-4,5,6,7-tetrahydrobenzo[b]thiophene with β-dimethylaminoethylamine. Dioxalate: white crystals; m.p. 222° C. (recrystallised from methanol/water); yield: 28% of theory.

EXAMPLE 19

E-4-(2-Hydroxy-3-isopropylaminopropoxy)-imino-5,6,7,8-tetrahydro-4H-cyclohepta[b]thiophene (I) (R$^1$=H, R$^2$=iPr; n=3)

This compound is prepared by the procedure described in Example 1 by condensing E-4-(2,3-epoxypropoxy)imino-5,6,7,8-tetrahydro-4H-cyclohepta[b]thiophene with isopropylamine. Hemioxalate: white crystals; m.p. 176° C. (recrystallised from acetone/ethanol; yield: 18% of theory.

EXAMPLE 20

E-4-(2-Hydroxy-3-isopropylaminopropoxy)-imino-5,6-dihydro-4H-cyclopenta[b]thiophene (I) (R$^1$=H, R$^2$=iPr; n=1)

This compound is prepared by the procedure described in Example 1 by condensing E-4-(2,3-epoxypropoxy)imino-5,6-dihydro-4H-cyclopenta[b]thiophene with isopropylamine. Hemioxalate: white crystals; m.p. 216° C. (recrystallised from methanol); yield: 61% of theory.

EXAMPLE 21

Z-4-(2-Hydroxy-3-isopropylaminopropoxy)-imino-4,5,6,7-tetrahydrobenzo[b]thiophene (II) (R$^1$=H, R$^2$=iPr; n=2)

This compound is prepared by the procedure described in Example 1 by condensing Z-4-(2,3-epoxypropoxy)imino-4,5,6,7-tetrahydrobenzo[b]thiophene with isopropylamine. Oxalate: white crystals; m.p. 138° C. (recrystallised from isopropyl alcohol); yield: 20% of theory.

The results of the toxicological and pharmacological tests given below demonstrate the low toxicity and the good tolerance of the compounds of general formulae (I) and (II), as well as their activity, in particular their inhibiting action on β-adrenergic receptors and their antiarrhythmic action.

I. TOXICOLOGICAL STUDY

The compounds of general formulae (I) and (II) have an excellent tolerance and a low toxicity. Thus, the LD 50/24 hours/kg of body weight, determined on mice by the method of Miller and Tainter by intravenous administration, is 28.4 mg. for derivative No. 1, 39.2 mg. for derivative No. 2, 40.5 mg. for derivative No. 6, 123.4 mg. for derivative No. 7, 32.1 mg. for derivative No. 8, 74.9 mg. for derivative No. 9, 49.5 mg. for derivative No. 10, 22.2 mg. for derivative No. 12, 99.3 mg. for derivative No. 15, 32.4 mg. for derivative No. 16 and 84.4 mg. for derivative No. 18.

In addition, tests carried out to determine the acute, chronic, subchronic and retarded toxicity in different species of animals demonstrated neither a local nor general reaction, nor a disturbance of the biological controls regularly carried out, nor any anomaly in the microscopic and macroscopic tests carried out on the animals sacrificed and subjected to autopsy at the end of the experimental period. Furthermore, the derivatives of general formulae (I) and (II) do not have a teratogenic effect.

II. PHARMACOLOGICAL STUDY.

(1) Inhibiting action on β-adrenergic receptors (a) In vitro

This study was carried out on spontaneously beating, isolated guinea pig auricles, using the method of K. Saameli (Helv. Physiol. Acta, 25, 219–221/1967).

The right and left auricles are placed in modified, oxygenated Tyrode's solution at 30° C. and the variations in the amplitude of the contractions are recorded continuously. After 30 minutes, 0.5 ml. of a solution of adrenaline hydrochloride containing 2.5 μmols/ml. of adrenaline is added to the medium and the auricles are left in contact with the medium for one minute. The auricles are washed with Tyrode's solution and, 20 minutes thereafter, the substance to be tested is added at a given concentration; 20 minutes later, a further 0.5 ml. of the adrenaline solution is added. The following effects are thus determined: the action of the compounds tested on the amplitude of the contractions, i.e. their negative inotropic activity; and the inhibiting action of the compounds tested towards adrenaline on the level of the β-adrenergic receptors.

When added in various concentrations to the medium in which the isolated, spontaneously beating guinea pig auricles are immersed, the compounds of the present invention exert a distinct antagonistic effect against the positive inotropic action produced by adrenaline on the frequency and amplitude of the contractions. Thus, for example, for compound No. 1, we have found that when this compound is introduced into the medium at a concentration of 0.050 mg/liter, it reduces the amplitude of the contractions, measured before introduction of adrenaline into the medium, by more than 15%.

Furthermore, at a concentration of 0.05 mg./liter, this compound inhibits the positive inotropic effect of adrenaline by more than 50%, i.e. it reduces the amplitude of the contractions produced solely by adrenaline by more than 50%.

(b) In vivo

The experiments were carried out on dogs. 0.1 μg./kg. of isoprenaline is administered intravenously to animals anaesthetised by an intravenous injection of pentobarbital. Two minutes after the injection, the arterial pressure, the cardiac frequency and the force of contraction of the cardiac muscle are measured and the product to be tested is injected into the femoral vein. The various parameters are measured again and it is found that the compounds tested inhibit disturbances caused by isoprenaline and restore the cardiac activity to normal.

The results summarised below indicate the doses of the most active compounds according to the present invention which totally inhibit the effects of isoprenaline:

| Compound tested of Example No. | Effective dose in mg./kg. |
|---|---|
| 1 | 2.50 |
| 2 | 2.9 |
| 3 | 2.20 |
| 4 | 2.50 |
| 6 | 3.0 |
| 7 | 2.80 |
| 8 | 2.1 |
| 9 | 2.50 |
| 10 | 3.0 |
| 12 | 2.3 |
| 13 | 2.2 |
| 15 | 2.8 |
| 16 | 2.4 |
| 18 | 2.5 |

(2) Antiarrhythmic action

This activity was studied on dogs: the test involves ligaturing, in one stage, the interventricular anterior coronary artery (see A. S. Harris, Circulation, 1, (6), 1318/1950). The anoxia which results therefrom causes electrophysiological modifications in the myocardial cells, giving rise to ventricular tachycardia or polymorphic arrhythmia.

The disorders start about 4 hours after ligaturing, the peak being reached about 10 to 20 hours after the intervention. Return to normal is in general after 72 hours.

The antiarrhythmic substances to be tested are administered, during the period of maximum disorders, at a dose of 10 mg./kg.; we have found that the compounds of the present invention cause the artificially caused disorders in rhythm to disappear rapidly.

The present invention also provides pharmaceutical compositions containing at least one of the new compounds and/or at least one pharmaceuticaly acceptable salt thereof, in admixture with a solid or liquid pharmaceutical diluent or carrier.

For oral administration, the compositions can be in the form of tablets, coated tablets, capsules, drops or syrups. The composition can also be in a form suitable for rectal administration, for example in the form of suppositories. For parenteral administration, it can be in the form of an injectable solution.

Each unit dose advantageously contains from 0.005 to 0.100 g. of active principle, together with appropriate, pharmaceutically compatible excipients, and the daily dose may vary from 0.005 to 0.300 g., depending upon the age of the patient and the severity of the disease to be treated.

Some examples of pharmaceutical formulations of the compositions of the present invention are given below:

| | |
|---|---|
| 1. Tablets | |
| Compound of Example 2 | 0.010 g. |
| Excipients: | starch, talc, glucose, magnesium stearate. |
| 2. Coated tablets | |
| Compound of Example 4 | 0.025 g. |
| Excipients: | lactose, maize starch, polyvinylpyrrolidone, magnesium stearate, talc, gum arabic, shellac, castor oil, titanium oxide, white wax, carnauba wax. |
| 3. Capsules | |
| Compound of Example 7 | 0.020 g. |
| Excipients: | "Aerosil", talc, magnesium stearate ("Aerosil" is a Registered Trade Mark) |
| 4. Suppositories | |
| Compound of Example 12 | 0.050 g. |
| Excipients: | semi-synthetic triglycerides. |
| 5. Injectable solutions | |
| Compound of Example 20 | 0.025 g. |
| Excipient: | isotonic solution q.s.p. 5 ml. |

Because of their inhibiting action on beta-adrenergic receptors and their antiarrhythmic properties, the compounds of the invention, and their pharmaceutical compositions are useful in human therapy. Thus, they are advantageously administered in the treatment of rhythm disorders and of arterial hypertension.

Particularly, the compounds of the invention are valuable in the treatment and control of the cardiovascular system in humans, for instance in the control of heart rate and cardiac output. The compounds of the invention are also useful as antiarrhythmic drugs.

The pharmacological properties of beta-adregenic blocking agents, such as the traditional propanolol (and related drugs) are described, for instance, in *The Pharmacological Basis For Therapeutics* (5th ed, 1975), Goodman and Gilman, MacMillan Publishing Co., Inc., New York, N.Y. in Chapter 26, Drugs Inhibiting Adrenergic Nerves and Structures Innervated By Them, pages 531, 547-552. Their antiarrhythmic action is especially discussed on pages 699-700. These texts are incorporated herein by reference.

We claim:

1. Derivatives of 1-aminopropan-2-ol of the formulae:

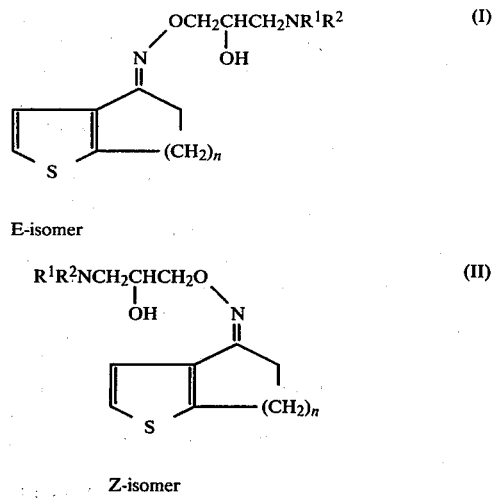

wherein R¹ and R², which can be the same or different, are hydrogen atoms, straight-chained or branched alkyl radicals containing up to 10 carbon atoms; mono- or polycyclic cycloalkyl radicals containing up to 14 carbon atoms and optionally substituted one or more times by alkyl radicals containing up to 4 carbon atoms; straight-chained or branched alkenyl radicals containing 3 to 7 carbon atoms; straight-chained or branched alkynyl radicals containing 3 to 7 carbon atoms; aryl radicals or aralkyl radicals containing up to 4 carbon atoms in the alkyl moiety, the aromatic nuclei being optionally substituted one or more times by halogen atoms or hydroxyl groups or alkyl or alkoxy radicals containing up to 4 carbon atoms; heteroaryl radicals or heteroaralkyl radicals containing up to 4 carbon atoms in the alkyl moiety; aminoalkyl radicals containing up to 4 carbon atoms and optionally mono- or di-substituted on the nitrogen atom by alkyl radicals containing up to 4 carbon atoms; alkoxyalkyl radicals; aralkoxyalkyl radicals; or aryloxyalkyl radicals; or R¹ and R², together with the nitrogen atom to which they are attached, form a heterocyclic radical containing 5 to 7 ring members and optionally containing another heteroatom selected from oxygen, sulphur and nitrogen, the nitrogen being optionally substituted by an alkyl radical containing up to 6 carbon atoms or by an aryl, aralkyl or aroyl radical, the aromatic nucleus of which is optionally mono- or polysubstituted by halogen atoms or hydroxyl groups; or alkyl or alkoxy radicals containing up to 4 carbon atoms; and n is 1, 2 or 3; and the addition salts thereof with pharmaceutically-acceptable inorganic or organic acids.

2. Derivatives of the general formulae given in claim 1, wherein R¹ and R², which may be the same or different, are hydrogen atoms; straight-chained or branched alkyl radicals containing up to 8 carbon atoms; monocyclic cycloalkyl radicals containing up to 12 carbon atoms or adamantyl radicals; α,α-dialkyl propynyl radicals, each alkyl moiety of which contains up to 4 carbon atoms; phenylalkyl radicals, the alkyl moiety of which contains up to 4 carbon atoms and the phenyl nucleus of which is optionally substituted one or more times by alkoxy radicals containing up to 4 carbon atoms; pyridylalkyl radicals containing up to 4 carbon atoms in the alkyl moiety; or dialkylaminoalkyl radicals, each alkyl moiety of which contains up to 4 carbon atoms; or R¹ and R², together with the nitrogen atom to which they are attached, form a pyrrolidino, morpholino or piperidino radical, the latter optionally being substituted on the other nitrogen atom by an alkyl radical containing up to 4 carbon atoms or by a benzyl radical; and n is 1, 2 or 3; and the addition salts thereof with pharmaceutically-acceptable inorganic or organic acids.

3. E-4-(3-tert.-Butylamino-2-hydroxypropoxy)-imino-4,5,6,7-tetrahydrobenzo[b]thiophene.

4. E-4-(2-Hydroxy-3-isopropylaminopropoxy)-imino-4,5,6,7-tetrahydrobenzo[b]thiophene.

5. E-4-(3-Cyclohexylamino-2-hydroxypropoxy)-imino-4,5,6,7-tetrahydrobenzo[b]thiophene.

6. E-4-[3-(Adamant-1-yl)-amino-2-hydroxypropoxy]imino-4,5,6,7-tetrahydrobenzo[b]thiophene.

7. E-4-(3-Cyclododecylamino-2-hydroxypropoxy)-imino-4,5,6,7-tetrahydrobenzo[b]thiophene.

8. E-4-[3-(1,1-Diethylprop-2-ynyl)-amino-2-hydroxypropoxy]-imino-4,5,6,7-tetrahydrobenzo[b]thiophene.

9. E-4-[2-Hydroxy-3-(4-methylpiperazin-1-yl)-propoxy]imino-4,5,6,7-tetrahydrobenzo[b]thiophene.

10. E-4-[2-Hydroxy-3-(pyrrolidin-1-yl)-propoxy]-imino-4,5,6,7-tetrahydrobenzo[b]thiophene.

11. E-4-(2-Hydroxy-3-morpholinopropoxy)-imino-4,5,6,7-tetrahydrobenzo[b]thiophene.

12. E-4-[2-Hydroxy-3-(3,4-dimethoxyphenethylamino)propoxy]-imino-4,5,6,7-tetrahydrobenzo[b]-thiophene.

13. E-4-(3-Benzylamino-2-hydroxypropoxy)-imino-4,5,6,7-tetrahydrobenzo[b]thiophene.

14. E-4-(2-Hydroxy-3-piperidinopropoxy)-imino-4,5,6,7-tetrahydrobenzo[b]thiophene.

15. E-4-[3-(4-Benzylpiperazin-1-yl)-2-hydroxypropoxy]-imino-4,5,6,7-tetrahydrobenzo[b]thiophene.

16. E-4-(2-Hydroxy-3-octylaminopropoxy)-imino-4,5,6,7-tetrahydrobenzo[b]thiophene.

17. E-4-[2-Hydroxy-3-(pyrid-3-ylmethyl)-aminopropoxy]-imino-4,5,6,7-tetrahydrobenzo[b]thiophene.

18. E-4-(3-Cyclopentylamino-2-hydroxypropoxy)-imino-4,5,6,7-tetrahydrobenzo[b]thiophene.

19. E-4-[3-(1,1-Dimethylprop-2-ynyl)-amino-2-hydroxypropoxy]-imino-4,5,6,7-tetrahydrobenzo[b]thiophene.

20. E-4-[2-Hydroxy-3-(β-dimethylaminoethylamino)-propoxy]-imino-4,5,6,7-tetrahydrobenzo[b]thiophene.

21. E-4-(2-Hydroxy-3-isopropylaminopropoxy)-imino-5,6,7,8-tetrahydro-4H-cyclohepta[b]thiophene.

22. E-4-(2-Hydroxy-3-isopropylaminopropoxy)-imino-5,6-dihydro-4H-cyclopenta[b]thiophene.

23. Z-4-(2-Hydroxy-3-isopropylaminopropoxy)-imino-4,5,6,7-tetrahydrobenzo[b]thiophene.

24. A pharmaceutical composition for use in the treatment and control of cardiac disorders in warm-blooded animals comprising an effective amount of at least one derivative according to claim 1 in admixture with a solid or liquid pharmaceutical diluent or carrier.

25. Pharmaceutical compositions according to claim 24, in a form suitable for oral, parenteral or rectal administration.

26. Pharmaceutical compositions according to claim 24 or 25 in the form of a dosage unit containing 0.005 to 0.100 g. of at least one derivative according to claim 1.

27. The pharmaceutical composition as defined in claim 24 wherein the derivative is E-4-(3-tert.-Butylamino-2-hydroxypropoxy)-imino-4,5,6,7-tetrahydrobenzo[b]thiopene.

28. The pharmaceutical composition as defined in claim 24 wherein the derivative is E-4-(2-Hydroxy-3-isopropylaminopropoxy)-imino-4,5,6,7-tetrahydrobenzo[b]thiophene.

29. The pharmaceutical composition as defined in claim 24 wherein the derivative is E-4-(3-Cyclohexylamino-2-hydroxypropoxy)-imino-4,5,6,7-tetrahydrobenzo[b]thiophene.

30. The pharmaceutical composition as defined in claim 24 wherein the derivative is E-4-[3-(Adamant-1-yl)-amino-2-hydroxypropoxy]-imino-4,5,6,7-tetrahydrobenzo[b]thiophene.

31. The pharmaceutical composition as defined in claim 24 wherein the derivative is E-4-(3-Cyclododecylamino-2-hydroxypropoxy)-imino-4,5,6,7-tetrahydrobenzo[b]thiophene.

32. The pharmaceutical composition as defined in claim 24 wherein the derivative is E-4-[3-(1,1-Diethylprop-2-ynyl)-amino-2-hydroxy-propoxyl]-imino-4,5,6,7-tetrahydrobenzo[b]thiophene.

33. The pharmaceutical composition as defined in claim 24 wherein the derivative is E-4-[2-Hydroxy-3-(4-methylpiperazin-1-yl)-propoxy]-imino-4,5,6,7-tetrahydrobenzo[b]thiophene.

34. The pharmaceutical composition as defined in claim 24 wherein the derivative is E-4-[2-Hydroxy-3-(pyrrolidin-1-yl)-propoxy]-imino-4,5,6,7-tetrahydrobenzo[b]thiophene.

35. The pharmaceutical composition as defined in claim 24 wherein the derivative is E-4-(2-Hydroxy-3-morpholinopropoxy)-imino-4,5,6,7-tetrahydrobenzo[b]thiophene.

36. The pharmaceutical composition as defined in claim 24 wherein the derivative is E-4-[2-Hydroxy-3-(3,4-dimethoxyphenethylamino)-propoxy]-imino-4,5,6,7-tetrahydrobenzo[b]thiophene.

37. The pharmaceutical composition as defined in claim 24 wherein the derivative is E-4-(3-Benzylamino-2-hydroxypropoxy)-imino-4,5,6,7-tetrahydrobenzo[b]thiophene.

38. The pharmaceutical composition as defined in claim 34 wherein the derivative is E-4-(2-Hydroxy-3-piperidinopropoxy)-imino-4,5,6,7-tetrahydrobenzo[b]thiophene.

39. The pharmaceutical composition as defined in claim 24 wherein the derivative is E-4-[3-(4-Benzylpiperazin-1-yl)-2-hydroxypropoxy]-imino-4,5,6,7-tetrahydrobenzo[b]thiophene.

40. The pharmaceutical composition as defined in claim 24 wherein the derivative is E-4-(2-Hydroxy-3-octylaminopropoxy)-imino-4,5,6,7-tetrahydrobenzo[b]thiophene.

41. The pharmaceutical composition as defined in claim 24 wherein the derivative is E-4-[2-Hydroxy-3-(pyrid-3-ylmethyl)-aminopropoxy]-imino-4,5,6,7-tetrahydrobenzo[b]thiophene.

42. The pharmaceutical composition as defined in claim 24 wherein the derivative is E-4-(3-Cyclopentylamino-2-hydroxypropoxy)-imino-4,5,6,7-tetrahydrobenzo[b]thiophene.

43. The pharmaceutical composition as defined in claim 24 wherein the derivative is E-4-[3-(1,1-Dimethylprop-2-ynyl)-amino-2-hydroxy-propoxy]-imino-4,5,6,7-tetrahydrobeno[b]thiophene.

44. The pharmaceutical composition as defined in claim 24 wherein the derivative is E-4-[2-Hydroxy-3-(-dimethylaminoethylamino)-propoxy]-imino-4,5,6,7-tetrahydrobenzo[b]thiophene.

45. The pharmaceutical composition as defined in claim 24 wherein the derivative is E-4-(2-Hydroxy-3-isopropylaminopropoxy)-imino-5,6,7,8-tetrahydro-4H-cyclohepta[b]thiophene.

46. The pharmaceutical composition as defined in claim 26 wherein the derivative is E-4-(2-Hydroxy-3-isopropylaminopropoxy)-imino-5,6-dihydro-4H-cyclopenta[b]thiophene.

47. The pharmaceutical composition as defined in claim 24 wherein the derivative is Z-4-(2-Hydroxy-3-isopropylaminopropoxy)-imino-4,5,6,7-tetrahydrobenzo[b]thiophene.

* * * * *